(12) United States Patent
Rinker et al.

(10) Patent No.: US 11,298,324 B2
(45) Date of Patent: *Apr. 12, 2022

(54) RAPIDLY DISINTEGRATING GELATINOUS COATED TABLETS

(71) Applicant: Johnson & Johnson Consumer inc., Skillman, NJ (US)

(72) Inventors: Roger A Rinker, Hatfield, PA (US); Nicholas J. Casale, Horsham, PA (US); James H. Comly, Downingtown, PA (US); Brenda Pollock, Cupertino, CA (US); Johan Geerke, Los Altos, CA (US); Martin Costello, Fremont, CA (US); Dennis Wieand, Coopersburg, PA (US); Kishor Parekh, Horsham, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/823,058

(22) Filed: Mar. 18, 2020

(65) Prior Publication Data

US 2020/0214986 A1 Jul. 9, 2020
US 2021/0393535 A9 Dec. 23, 2021

Related U.S. Application Data

(60) Continuation of application No. 16/116,216, filed on Aug. 29, 2018, now Pat. No. 10,632,078, which is a continuation of application No. 14/833,839, filed on Aug. 24, 2015, now Pat. No. 10,092,521, which is a continuation of application No. 14/335,228, filed on Jul. 18, 2014, now Pat. No. 9,149,438, which is a continuation of application No. 12/970,079, filed on Dec. 16, 2010, now Pat. No. 8,815,290, which is a division of application No. 10/756,528, filed on Jan. 13, 2004, now Pat. No. 7,879,354.

(51) Int. Cl.
*A61K 9/28* (2006.01)
*A61K 9/20* (2006.01)
*A61K 31/167* (2006.01)
*A61K 45/06* (2006.01)

(52) U.S. Cl.
CPC .......... *A61K 9/2886* (2013.01); *A61K 9/2072* (2013.01); *A61K 9/286* (2013.01); *A61K 9/2866* (2013.01); *A61K 9/2873* (2013.01); *A61K 31/167* (2013.01); *A61K 45/06* (2013.01)

(58) Field of Classification Search
CPC .... A61K 45/06; A61K 9/2072; A61K 9/2866; A61K 9/2873; A61K 31/167; A61K 9/286; A61K 9/2886
See application file for complete search history.

(56) References Cited

U.S. PATENT DOCUMENTS

| | | |
|---|---|---|
| 3,185,626 A | 5/1965 | Baker |
| 3,760,804 A | 9/1973 | Higuchi et al. |
| 3,823,816 A | 7/1974 | Controulis et al. |
| 4,173,626 A | 11/1979 | Dempski et al. |
| 4,279,926 A | 7/1981 | Bruzzese et al. |
| 4,449,983 A | 5/1984 | Cortese et al. |
| 4,511,553 A | 4/1985 | Boesig et al. |
| 4,543,370 A | 9/1985 | Porter et al. |
| 4,576,604 A | 3/1986 | Guittard et al. |
| 4,643,894 A | 2/1987 | Porter et al. |
| 4,683,256 A | 7/1987 | Porter et al. |
| 4,725,441 A | 2/1988 | Porter et al. |
| 4,802,924 A | 2/1989 | Woznicki et al. |
| 4,816,262 A | 3/1989 | McMullen |
| 4,820,524 A | 4/1989 | Berta |
| 4,828,841 A | 5/1989 | Porter et al. |
| 4,863,742 A | 9/1989 | Panoz et al. |
| 4,867,983 A | 9/1989 | Berta |
| 4,873,231 A | 10/1989 | Smith |
| 4,906,478 A | 3/1990 | Valentine et al. |
| 4,965,089 A | 10/1990 | Sauter et al. |
| 4,966,771 A | 10/1990 | Berta |
| 4,980,170 A | 12/1990 | Schneider et al. |
| 4,984,240 A | 1/1991 | Keren-Zvi et al. |
| 5,004,614 A | 4/1991 | Staniforth |
| 5,089,270 A | 2/1992 | Hampton et al. |
| 5,114,720 A | 5/1992 | Littel et al. |
| 5,146,730 A | 9/1992 | Sadek et al. |
| 5,213,738 A | 5/1993 | Hampton et al. |

(Continued)

FOREIGN PATENT DOCUMENTS

| CN | 1265587 A | 9/2000 |
|---|---|---|
| EP | 279682 A2 | 8/1988 |

(Continued)

OTHER PUBLICATIONS

Elizabeth Carbide Die Co. Inc., The Elizabeth Companies Tablet Design Training Manual, p. 7, McKeesport, PA.
Eith, L., et al. "Injection-Moulded Drug Delivery Systems", Manufacturing Chemist (Jan. 1987), pp. 21-25.
Lachman et al. The theory and Practice of Industrial Pharmacy, 1986, Chapter 11, 3rd Ed.

(Continued)

*Primary Examiner* — Michael G. Hartley
*Assistant Examiner* — Leah H Schlientz
(74) *Attorney, Agent, or Firm* — Laura A. Donnelly

(57) ABSTRACT

The present invention relates to an improved gelatinous coated dosage form having two end regions coated with gelatinous materials and an exposed circumferential band. Openings are provided in at least the exposed band to reveal the core material. The invention also relates to methods for manufacturing such gelatinous coated dosage forms.

10 Claims, 1 Drawing Sheet

(56) References Cited

U.S. PATENT DOCUMENTS

| | | |
|---|---|---|
| 5,228,916 A | 7/1993 | Berta |
| 5,234,099 A | 8/1993 | Berta |
| 5,256,440 A | 10/1993 | Appel et al. |
| 5,275,822 A | 1/1994 | Valentine et al. |
| 5,317,849 A | 6/1994 | Sauter |
| 5,415,868 A | 5/1995 | Smith et al. |
| 5,424,075 A | 6/1995 | Daher et al. |
| 5,427,614 A | 6/1995 | Wittwer et al. |
| 5,436,026 A | 7/1995 | Berta |
| 5,459,983 A | 10/1995 | Sadek et al. |
| 5,460,824 A | 10/1995 | LeBrun et al. |
| 5,464,631 A | 11/1995 | Hoover et al. |
| 5,498,255 A | 3/1996 | Wong |
| 5,510,385 A | 4/1996 | Stroppolo et al. |
| 5,511,361 A | 4/1996 | Sauter |
| 5,538,125 A | 7/1996 | Berta |
| 5,582,838 A | 12/1996 | Rork et al. |
| 5,609,010 A | 3/1997 | Sauter |
| 5,630,871 A | 5/1997 | Jordan |
| 5,658,589 A | 8/1997 | Parekh et al. |
| 5,679,406 A | 10/1997 | Berta |
| 5,795,588 A | 8/1998 | Sauter |
| 5,824,338 A | 10/1998 | Jacobs et al. |
| 5,912,013 A | 6/1999 | Rudnic et al. |
| 5,942,034 A | 8/1999 | Brehant et al. |
| 6,080,426 A | 6/2000 | Amey et al. |
| 6,103,260 A | 8/2000 | Luber et al. |
| 6,110,499 A | 8/2000 | Shivanand et al. |
| 6,126,767 A | 10/2000 | Smith et al. |
| 6,126,987 A | 10/2000 | Brehaut et al. |
| 6,245,350 B1 | 6/2001 | Amey et al. |
| 6,264,985 B1 | 7/2001 | Cremer |
| 6,270,805 B1 | 8/2001 | Chen et al. |
| 6,274,162 B1 | 8/2001 | Steffenino et al. |
| 6,322,816 B1 | 11/2001 | Zeidler et al. |
| 6,322,819 B1 | 11/2001 | Burnside et al. |
| 6,365,185 B1 | 4/2002 | Ritschel et al. |
| 6,471,994 B1 | 10/2002 | Staniforth et al. |
| 6,479,551 B1 | 11/2002 | Plachetka et al. |
| 6,599,532 B2 | 7/2003 | Faour et al. |
| 6,696,085 B2 | 2/2004 | Rault et al. |
| 6,742,646 B2 | 6/2004 | Sowden et al. |
| 6,767,200 B2 | 7/2004 | Sowden et al. |
| 6,837,696 B2 | 1/2005 | Sowden et al. |
| 6,872,405 B2 | 3/2005 | Takaishi et al. |
| 6,946,156 B2 | 9/2005 | Bunick |
| 6,982,094 B2 | 1/2006 | Sowden |
| 7,122,143 B2 | 1/2006 | Sowden |
| 7,169,450 B2 | 1/2007 | Bunick |
| 2002/0004472 A1 | 1/2002 | Holderbaum et al. |
| 2002/0028240 A1 | 3/2002 | Sawada et al. |
| 2002/0031552 A1 | 3/2002 | McTeigue et al. |
| 2002/0051807 A1 | 5/2002 | Faour et al. |
| 2002/0119196 A1* | 8/2002 | Parikh ............ A61K 9/0056 424/472 |
| 2003/0068367 A1 | 4/2003 | Sowden |
| 2003/0070584 A1 | 4/2003 | Gulian et al. |
| 2003/0070903 A1 | 4/2003 | Sowden |
| 2003/0072731 A1 | 4/2003 | Gulian et al. |
| 2003/0072799 A1 | 4/2003 | Sowden |
| 2003/0086973 A1 | 5/2003 | Sowden |
| 2003/0108607 A1 | 6/2003 | Szymczak |
| 2003/0124183 A1 | 7/2003 | Sowden |
| 2003/0215563 A1 | 11/2003 | Bunick |
| 2003/0215585 A1 | 11/2003 | Bunick |
| 2004/0022755 A1 | 2/2004 | Kamath |
| 2004/0062804 A1 | 4/2004 | Sowden |
| 2004/0062806 A1 | 4/2004 | Martini et al. |
| 2004/0253312 A1 | 12/2004 | Sowden et al. |
| 2005/0152970 A1 | 7/2005 | Rinker et al. |
| 2005/0152971 A1 | 7/2005 | Rinker et al. |

FOREIGN PATENT DOCUMENTS

| | | |
|---|---|---|
| EP | 325492 A1 | 7/1989 |
| EP | 1440790 A1 | 7/2004 |
| GB | 759081 | 10/1956 |
| WO | WO 95/02395 A | 1/1995 |
| WO | WO 97/37629 | 10/1997 |
| WO | WO 99/06038 | 2/1999 |
| WO | WO 99/62496 A | 12/1999 |
| WO | WO 01/51040 | 7/2001 |
| WO | WO 01/57144 A1 | 8/2001 |
| WO | WO 02/11702 A2 | 2/2002 |
| WO | WO 02/38131 | 5/2002 |
| WO | WO 03020246 A1 | 3/2003 |
| WO | WO 03/068195 A | 8/2003 |
| WO | WO 04/028513 A | 4/2004 |
| WO | WO 04/073582 A2 | 9/2004 |

OTHER PUBLICATIONS

Leiberman et al., Pharmaceutical Dosage Forms—Tablets, 1990, pp. 213-217, 327-329, vol. 2, 2nd Edition., Marcel Dekker, Inc.

Fegley et al., The Effect of Tablet Shape on the Perception of High Gloss Film Coating Systems, www.colorcon.com. Mar. 18, 2002.

Remington's Pharmaceutical Sciences (17th Ed. 1985), pp. 1633-1636.

The United States Pharmacopeia, The National formulary, 2000 USP24/NF19 (1999), pp. 19, 202, 856.

PCT Search Report for PCT/US2005/001075 dated Jun. 22, 2005.

European Search Report : EP 05 25 3398 dated Oct. 19, 2005.

PCT Search Report for PCT/US2003/08897 dated Aug. 19, 2003.

PCT Search Report PCT/US03/08891 dated Jan. 8, 2004.

* cited by examiner

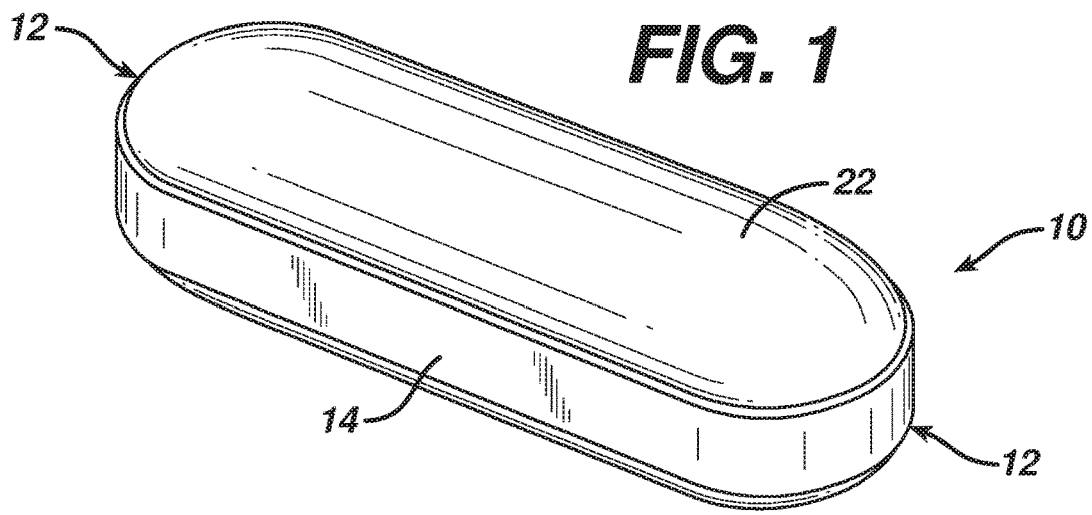
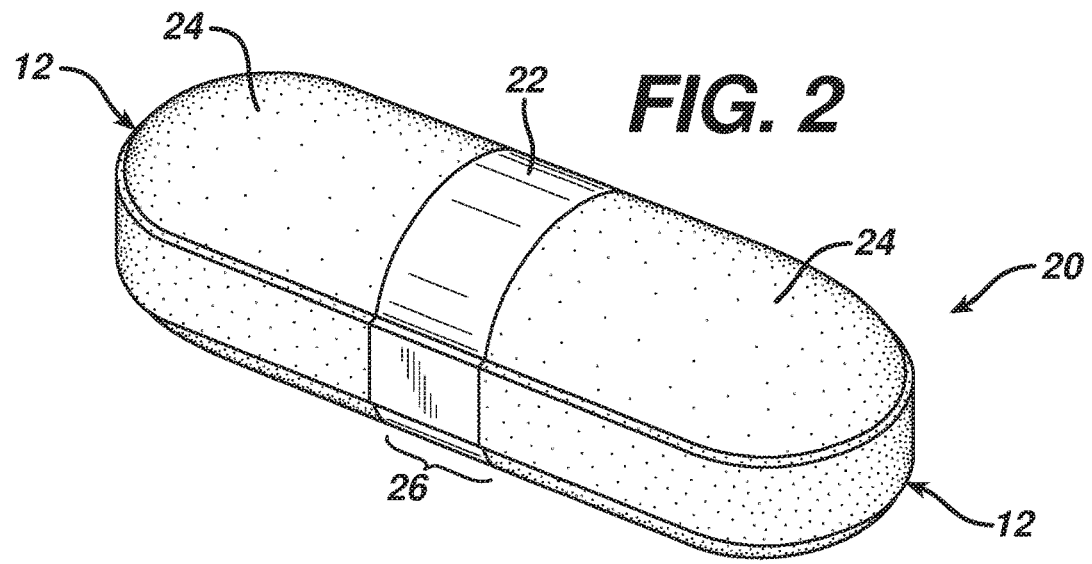
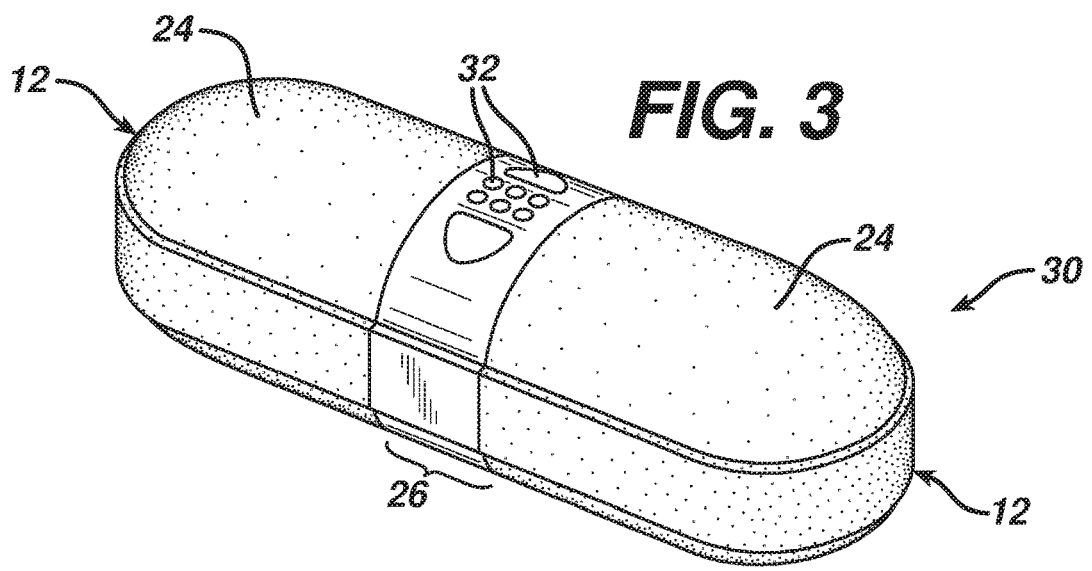

RAPIDLY DISINTEGRATING GELATINOUS COATED TABLETS

RELATED APPLICATIONS

This application, which is a continuation application, claims priority of the benefit of U.S. patent application Ser. No. 16/116,216, filed Aug. 29, 2018; U.S. patent application Ser. No. 14/833,839, filed Aug. 24, 2015 (now U.S. Pat. No. 10,092,521); U.S. patent application Ser. No. 14/335,228, filed Jul. 18, 2014 (now U.S. Pat. No. 9,149,438); U.S. patent application Ser. No. 12/970,079, filed Dec. 16, 2010 (now U.S. Pat. No. 8,815,290); and U.S. patent application Ser. No. 10/756,528, filed Jan. 13, 2004 (now U.S. Pat. No. 7,879,354). The complete disclosures of the aforementioned U.S. patent applications are incorporated by reference in their entirety herein for all purposes.

The present invention relates to a dosage form comprising a tablet core having two ends. The tablet core, preferably in compressed form, is provided with a polymeric subcoating over its exterior surface. Further, the dosage form includes gelatinous coatings over both ends. The gelatinous endcaps are provided on opposing ends of the elongated tablet core or opposing sides of a round tablet core so that they do not meet and form a circumferential gap or band through which the subcoating is visible. Openings are provided in the dosage form that extend through the subcoat to the exterior surface of the elongated tablet or round tablet core. The openings are preferably provided only in the exposed gap of the subcoatings.

BACKGROUND OF THE INVENTION

Capsules have long been recognized as a preferred dosage form for the oral delivery of active ingredients, which may be in the form of powder, liquid or granules of different compositions, for delivery to the gastro-intestinal tract of a human. Advantages of capsules as a dosage form include the variety of shapes and color combinations (including different colored caps and bodies), enhancing their unique identification, their glossy elegant appearance, and their easy swallowability. One type of commonly used capsule is a two-piece hard shell capsule, typically made from gelatin, starch, or cellulose derivatives. The hard shell capsule typically comprises a longer body having an outside diameter, and a relatively shorter cap having an inside diameter that will just fit over the outside diameter of the body. The cap fits snugly over the body, creating an overlapping portion of the capsule.

In view of the tamperability of old-fashioned capsules made with hard shell capsule halves of different diameters which can be taken apart, steps have been taken since the 1980s, to manufacture capsule shells which, once assembled, cannot be disassembled without their destruction. One such example is the Capsugel CONI-SNAP® capsule, which has grooves that lock the cap and body together after the capsule has been filled. Another such example is the Parke-Davis KAPSEAL® capsule, in which the body and cap are sealed together using a band of gelatin. Although the sealing or banding of capsule shell halves has, in a large part, proven effective to at least make tampering evident to the consumer, some companies have preferred to manufacture solid dosage forms having densely compacted cores to further reduce the possibility of tampering.

One of the first types of film-coated elongated compressed tablets was referred to as a "caplet". The caplet form offered enhanced swallowability over uncoated tablets due to its elongated shape and film-coated surface, similar to that of the capsule. It did not, however, enable the multi-colored glossy surface appearance of a capsule. While caplets are still popular today, the next generation of dosage forms, which offered all of these advantages of the capsule, comprised densely compacted cores that were coated with gelatin or similar glossy materials, typically in two parts having different colors. U.S. Pat. Nos. 5,089,270; 5,213,738; 4,820,524; 4,867,983 and 4,966,771 represent different approaches to providing a capsule-shaped product in the form of an elongated tablet having a coating, which provides the appearance and, therefore, the consumer acceptability of the previously popular capsule.

U.S. Pat. Nos. 5,415,868 and 5,317,849 disclose different manners by which either hard shell capsule halves can be shrink-wrapped onto a tablet (the '868 patent) or a tablet core covered at opposite ends with a soft gelatin capsule shell half and subsequently dried to simulate a capsule-like medicament (the '849 patent). U.S. Pat. No. 5,464,631 suggests that studies have also shown the functional importance to consumers of providing a capsule-appearing solid dosage form, which is multi-colored. The utilization of two colors functionally identifies the type of medication as well as provides a capsule-appearing product with a psychologically perceived medicinal efficacy. Aesthetically, also, consumers apparently prefer the attractive appearance of multi-colored capsules to single colored capsules.

Thus, there has been a rush by the pharmaceutical industry to provide over-the-counter gelatinous coated dosage forms which simulate the appearance of capsules and which have a variety of multiple colors which identify the type of medication provided so that the consumer can readily identify, for example, if the product is a particular type of analgesic or whether it includes antihistamines or other active ingredients in combination with analgesics. Such solid dosage forms have preferably been in the shape of an elongated tablet, and are identified as gelcaps when a solid elongated core is covered with a gelatinous covering or geltabs where the core is in the shape of a round tablet with a gelatinous coating.

The present invention furthers these earlier advances by producing an improved gelcap or geltab having faster disintegration and/or dissolution times relative to the commercially available gelatinous coated products.

BRIEF DESCRIPTION OF THE DRAWINGS

FIG. 1 is an enlarged isometric view of a compressed core in the form of an elongated tablet having a generally cylindrical shape, called a "gelcap core".

FIG. 2 is an enlarged isometric view of an intermediate dosage form.

FIG. 3 is a final dosage form of the present invention.

DETAILED DESCRIPTION OF INVENTION

As used herein, the term "dosage form" applies to any solid object, semi-solid, or liquid composition designed to contain a specific pre-determined amount (dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human. In another preferred embodiment, the dosage form is an orally administered "placebo" system containing pharmaceutically inactive ingredients, and the dosage form is designed to have the same appearance as a particular pharmaceutically active dosage form, such as may be used for control purposes in clinical studies to test, for example, the safety and efficacy of a particular pharmaceutically active ingredient.

As used herein the term "tablet" refers to a solid form prepared by compaction of powders on a tablet press, as well known in the pharmaceutical arts. Tablets can be made in a variety of shapes, including round, or elongated, such as flattened ovoid or cylindrical shapes. As used herein, a "gelcap core" refers to one type of elongated, generally cylindrical or capsule-shaped tablet having straight or slightly bowed sides, and a generally circular cross-section, and having a length to diameter ratio from about 2 to about 5, e.g. from about 2.5 to about 3.5, say about 3.

A caplet is one type of elongated tablet covered by a film coating. There is shown in FIG. 1 a core 10 in the shape of an elongated tablet having two ends 12 at opposing sides of a longitudinal axis. A bellyband 14 occurs along the longitudinal circumference where the tablet is in contact with the die walls during compaction.

The core can have any number of pharmaceutically acceptable tablet shapes. Tablet is meant to encompass shaped compacted dosage forms in the broadest sense. An elongated tablet is a type of tablet having an elongated shape. One type of gelcap core shown in FIG. 1 has a generally circular cross section that generally tapers from the mid-section to a tip or end region. For purposes of this application, the longitudinal axis passes through the center of both ends of the gelcap core.

The core (or substrate) may be any solid or semi-solid form. The core may prepared by any suitable method, for example the core be a compressed dosage form, or may be molded. As used herein, "substrate" refers to a surface or underlying support, upon which another substance resides or acts, and "core" refers to a material that is at least partially enveloped or surrounded by another material. For the purposes of the present invention, the terms may be used interchangeably: i.e. the term "core" may also be used to refer to a "substrate." Preferably, the core comprises a solid, for example, the core may be a compressed or molded tablet, hard or soft capsule, suppository, or a confectionery form such as a lozenge, nougat, caramel, fondant, or fat based composition. In certain other embodiments, the core may be in the form of a semi-solid or a liquid in the finished dosage form.

In one embodiment, the core has one or more major faces. The core may be in a variety of different shapes. For example, in one embodiment the core may be in the shape of a truncated cone. In other embodiments the core may be shaped as a polyhedron, such as a cube, pyramid, prism, or the like; or may have the geometry of a space figure with some non-flat faces, such as a cone, cylinder, sphere, torus, or the like. Exemplary core shapes that may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling):

Shallow Concave.
Standard Concave.
Deep Concave.
Extra Deep Concave.
Modified Ball Concave. Standard
Concave Bisect. Standard
Concave Double Bisect.
Standard Concave European Bisect.
Standard Concave Partial Bisect.
Double Radius.
Bevel & Concave.
Flat Plain.
Flat-Faced-Beveled Edge (F.F.B.E.).
F.F.B.E. Bisect.
F.F.B.E. Double Bisect.
Ring.
Dimple.
Ellipse.
Oval.
Capsule.
Rectangle.
Square.
Triangle.
Hexagon.
Pentagon.
Octagon.
Diamond.
Arrowhead.
Bullet.
Barrel.
HalfMoon.
Shield.
Heart. Almond.
House/Home Plate.
Parallelogram.
Trapezoid.
Figure 8/Bar Bell.
Bow Tie.
Uneven Triangle.

Core 10 is pressed of a blend of suitable active ingredients and excipients which may be either their natural color, including white, or can be conventionally colored as desired to provide a conventional, or elongated-shaped core of any desired color.

The dosage form of the present invention preferably contains one or more active ingredients. Suitable active ingredients broadly include, for example, pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for H. pylori, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

In one embodiment of the invention, at least one active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, at least one active ingredient is selected from analgesics, anti-inflammatories, and antipyretics, e.g. non-steroidal anti-inflammatory drugs (NSAIDs), including a) propionic acid derivatives, e.g. ibuprofen, naproxen, ketoprofen and the like; b) acetic acid derivatives, e.g. indomethacin, diclofenac, sulindac, tolmetin, and the like; c) fenamic acid derivatives, e.g. mefenamic acid, meclofenamic acid, flufenamic acid, and the like; d) biphenylcarbodylic acid derivatives, e.g. diflunisal, flufenisal, and the like; e) oxicams, e.g. piroxicam, sudoxicam, isoxicam, meloxicam, and the like; f) cyclooxygenase-2 (COX-2) selective NSAIDs; and g) pharmaceutically acceptable salts of the foregoing.

In one particular embodiment, at least one active ingredient is selected from propionic acid derivative NSAID, which are pharmaceutically acceptable analgesics/non-steroidal anti-inflammatory drugs having a free —$CH(CH_3)$COOH or —$CH_2CH_2COOH$ or a pharmaceutically acceptable salt group, such as —$CH(CH_3)COO$—Na+ or $CH_2CH_2COO$—Na+, which are typically attached directly or via a carbonyl functionality to a ring system, preferably an aromatic ring system.

Examples of useful propionic acid derivatives include ibuprofen, naproxen, benoxaprofen, naproxen sodium, fenbufen, flurbiprofen, fenoprofen, fenbuprofen, ketoprofen, indoprofen, pirprofen, carpofen, oxaprofen, pranoprofen, microprofen, tioxaprofen, suprofen, alminoprofen, tiaprofenic acid, fluprofen, bucloxic acid, and pharmaceutically acceptable salts, derivatives, and combinations thereof. In one embodiment of the invention, the propionic acid derivative is selected from ibuprofen, ketoprofen, flubiprofen, and pharmaceutically acceptable salts and combinations thereof. In another embodiment, the propionic acid derivative is ibuprofen, 2-(4-isobutylphenyl) propionic acid, or a pharmaceutically acceptable salt thereof, such as the arginine, lysine, or histidine salt of ibuprofen. Other pharmaceutically acceptable salts of ibuprofen are described in U.S. Pat. Nos. 4,279,926, 4,873,231, 5,424,075 and 5,510,385, the contents of which are incorporated by reference.

In another particular embodiment of the invention, at least one active ingredient may be an analgesic selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another particular embodiment of the invention, at least one active ingredient may be selected from pseudoephedrine, phenylpropanolamine, chlorpheniramine, dextromethorphan, diphenhydramine, astemizole, terfenadine, fexofenadine, loratadine, desloratadine, cetirizine, mixtures thereof and pharmaceutically acceptable salts, esters, isomers, and mixtures thereof.

In another particular embodiment, at least one active ingredient is an NSAID and/or acetaminophen, and pharmaceutically acceptable salts thereof.

The active ingredient or ingredients are present in the dosage form in a therapeutically effective amount, which is an amount that produces the desired therapeutic response upon oral administration and can be readily determined by one skilled in the art. Indetermining such amounts, the particular active ingredient being administered, the bioavailability characteristics of the active ingredient, the dosing regimen, the age and weight of the patient, and other factors must be considered, as known in the art. Typically, the dosage form comprises at least about 1 weight percent, preferably, the dosage form comprises at least about 5 weight percent, e.g. about 20 weight percent of a combination of one or more active ingredients. In one preferred embodiment, the core comprises a total of at least about 25 weight percent (based on the weight of the core) of one or more active ingredients.

The active ingredient or ingredients may be present in the dosage form in any form. For example, one or more active ingredients may be dispersed at the molecular level, e.g. melted or dissolved, within the dosage form, or may be in the form of particles, which in turn may be coated or uncoated. If an active ingredient is in form of particles, the particles (whether coated or uncoated) typically have an average particle size of about 1-2000 microns. In one preferred embodiment, such particles are crystals having an average particle size of about 1-300 microns. In another preferred embodiment, the particles are granules or pellets having an average particle size of about 50-2000 microns, preferably about 50-1000 microns, most preferably about 100-800 microns.

In certain embodiments, at least a portion of one or more active ingredients may be optionally coated with a release modifying coating, as known in the art. This advantageously provides an additional tool for modifying the release profile of active ingredient from the dosage form. For example, the core may contain coated particles of one or more active ingredients, in which the particle coating confers a release modifying function, as is well known in the art. Examples of suitable release modifying coatings for particles are described in U.S. Pat. Nos. 4,173,626; 4,863,742; 4,980,170; 4,984,240; 5,86,497; 5,912,013; 6,270,805; and 6,322,819. Commercially available modified release coated active particles may also be employed. Accordingly, all or a portion of one or more active ingredients in the core may be coated with a release-modifying material.

In embodiments in which it is desired for at least one active ingredient to be absorbed into the systemic circulation of an animal, the active ingredient or ingredients are preferably capable of dissolution upon contact with a dissolution medium such as water, gastric fluid, intestinal fluid or the like.

In one embodiment, the dissolution characteristics of at least one active ingredient meets USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In embodiments in which at least one active ingredient is released immediately, the immediately released active ingredient is preferably contained in the shell or on the surface of the shell, e.g. in a further coating surrounding at least a portion of the shell.

In another embodiment, the dissolution characteristics of one or more active ingredients are modified: e.g. controlled, sustained, extended, retarded, prolonged, delayed and the like. In a preferred embodiment in which one or more active ingredients are released in a modified manner, the modified release active or actives are preferably contained in the core. As used herein, the term "modified release" means the release of an active ingredient from a dosage form or a portion thereof in other than an immediate release fashion, i.e., other than immediately upon contact of the dosage form or portion thereof with a liquid medium. As known in the art, types of modified release include delayed or controlled. Types of controlled release include prolonged, sustained, extended, retarded, and the like. Modified release profiles that incorporate a delayed release feature include pulsatile, repeat action, and the like. As is also known in the art, suitable mechanisms for achieving modified release of an active ingredient include diffusion, erosion, surface area control via geometry and/or impermeable or semi-permeable barriers, and other known mechanisms.

In certain preferred embodiments, the core 10 is subsequently covered with a subcoating 12 that can be any number of medicinally acceptable coverings. The use of subcoatings is well known in the art and disclosed in, for example, U.S. Pat. No. 5,234,099, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643,894, 4,828,841, 4,725,441,4,802,924, 5,630,871, and 6,274,162, which are all incorporated by reference herein. Suitable compositions for use as subcoatings include those manufactured by Colorcon, a division of Berwind Pharmaceutical Services, Inc., 415 Moyer Blvd., West Point, Pa. 19486 under the tradename "OPADRY®" (a dry concentrate comprising film forming polymer and optionally plasticizer, colorant, and other useful excipients). Additional suitable subcoatings include one or more of the following ingredients: cellulose ethers such as hydroxypropylmethylcellulose, hydroxypropy 1 cellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as Polysorbate-SO, sodium lauryl sulfate and dioctyl-sodium sulfosuccinate; polycarbohydrates, pigments, and opacifiers.

In one embodiment, the subcoating comprises from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating comprises from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400. The dried subcoating typically is present in an amount, based upon the dry weight of the core, from about 0 percent to about 5 percent. The subcoat is typically provided by spraying in a coating pan or fluidized bed to cover the tablet in a conventional manner. The subcoating composition is optionally tinted or colored with colorants such as pigments, dyes and mixtures thereof.

In one embodiment, subcoating 12 is initially applied to the entire exterior surface of core 10. Subcoating 12 can be applied as a clear, transparent coating such that the core can be seen. The choice is dictated by the preference of the manufacturer and the economics of the product. In a preferred embodiment, a commercially available pigment is included the subcoating composition in sufficient amounts to provide an opaque film having a visibly distinguishable color relative to the core.

An unexpected improvement resulting from the modified gel dipping process has been a change in subcoating requirements. The conventional amount of subcoating has been the use of sufficient amounts of subcoating for at least a 3.5%, typically at least a 4% weight gain (i.e. the weight of the coated core is 3.5 to 4% more than the weight of the uncoated core). Conventional gel-dipping processes required a subcoating weight gain of at least 3.5% to prevent unacceptable bubbling of the dip-coating (referred to herein as the gelatinous coating) and other processing problems. It has now been discovered that for dosage forms coated according to the present invention (in which the more than one non-overlapping gelatinous coatings are applied) the amount, as measured by weight gain, of subcoating can be reduced to not more than about 3%, e.g. not more than about 2.75%, or not more than about 2.5%, or not more than about 2.1%, say to about 2% weight gain and still produce acceptable gelatin coated dosage forms. Weight gain calculations are well known to those skilled in the art.

FIG. 2 illustrates an intermediate dosage form 20 having two ends 12 with gelatinous coatings 24 that do not abut or overlap one another. The gelatinous coatings 24 are separated from one another and create a gap 26. Subsequent to applying subcoating 22 onto core 10, both ends 12 of core 10 are covered with gelatinous coatings 24, preferably containing a colorant or coloring agent. The opposing ends 12 of dosage form 20 can be covered with clear gelatinous materials or gelatinous materials having the same color as core 10, the same color as the subcoating 22, a different color from the core 10 and/or subcoating 22, and may be the same or different from one another. Coloring of the gelatinous coating 24 may be the result of incorporating a suitable ink, dye or pigment into the gelatinous materials. In the preferred embodiment, sufficient pigment is employed to create an opaque colored coating.

In certain preferred embodiments of the invention the dosage form further comprises one, or more preferably a plurality of openings provided in the exposed portion of the subcoating. The openings may be of any shape and size, and may optionally be arranged in a pattern. In embodiments in which the openings are made by laser ablation, the width or diameter of the smallest opening is typically at least I-2 times the wavelength of light provided by the laser employed. At least a portion of the openings may be large enough to be seen with the unaided human eye, ranging in width or diameter from about 400 nanometers to as much as any dimension of the exposed subcoating. Typically, such openings will have minimum width or diameter of at least about 500 nanometers, e.g. at least about 700 nanometer, or at least about 70 microns.

Typically visible openings will have a maximum width or diameter of not more than the width of the tablet, or not more than the width of the exposed subcoating band, for example not more than about 6.5 millimeters, or not more than about 3.5 millimeters, say not more than about 2.5 millimeters. Alternatively, some or all of the openings may be microscopic in size, ranging from about 1 to less than about 400 nanometers in width or diameter. In embodiments in which some or all of the openings are invisible to the unaided human eye, a plurality of openings may be arranged in a pattern that creates perforations or weak spots in the film, which facilitate disintegration. While it is not critical to the invention that the initial openings be large enough to allow the influx of water, particularly when water-soluble subcoatings are employed, it should be noted that it has been found that for certain preferred embodiments, an opening size of about 0.030 inches in width or diameter will allow water to pass therethrough.

For purposes of this application, a gelatinous material is defined to be a material that, when applied by dip coating, produces a film coating having a surface gloss comparable to gelatin coatings. "Surface gloss" as used herein, shall refer to amount of light reflectance as measured at a sixty (60) degree incident angle using the method set forth in the examples. Preferably, the gelatinous coating has a surface gloss greater than about 150, more preferably greater than about 200.

Gelatins have traditionally served as a primary dip-coating material. Hence, the phrase "gelatinous" material. Recently, further work has been done to expand the range of materials capable of providing the desired glossy finish that contain substantially no gelatins.

Gelatin is a natural, thermogelling polymer. It is a tasteless and colorless mixture of derived proteins of the albuminous class, which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours.

In certain embodiments of the invention, the level of gelatin is from about 20% to about 50% by weight of the gelatinous material. In one particular such embodiment, the gelatin is a blend of gelatins in which a first portion has a Bloom value of about 275 and a second portion has a Bloom value of about 250 Bloom. In certain embodiment the level of gelatin in the dipping dispersion is from about 25% to about 45%, e.g. about 30 to about 40%, say about 33% by weight of the dipping dispersion. In such embodiments, the level of gelatin is from about 99% to about 99.9% by weight of the finished gelatinous coating.

Suitable water soluble, substantially gelatin-free, film forming compositions for dip coating tablets or manufacturing capsules via a dip molding process are described in copending application, Ser. No. 10/122,999, filed Apr. 12, 2002, published as US 2003-0070584 A1, which is incorporated herein by reference. One such gelatinous composition comprises, consists of, and/or consists essentially of a film former such as a cellulose ether, e.g., hydroxypropylmethylcellulose; and a thickener, such as a hydrocolloid, e.g., xanthan gum or carrageenan. In another embodiment, the gelatinous composition comprises, consists of, and/or consists essentially of a film former such as a modified starch selected from waxy maize starch, tapioca dextrin, and derivatives and mixtures thereof; a thickener selected from sucrose, dextrose, fructose, maltodextrin, polydextrose, and derivatives and mixtures thereof; and a plasticizer, e.g., polyethylene glycol, propylene glycol, vegetable oils such as castor oil, glycerin, and mixtures thereof.

In yet another embodiment, the gelatinous composition comprises, consists of, and/or consists essentially of a film former such as a cellulose ether, e.g., hydroxypropyl methylcellulose; and optionally a plasticizer, such as vegetable oils, e.g., castor oil; and may optionally be substantially free of thickeners such as hydrocolloids, e.g. xanthan gum. In yet another embodiment, the gelatinous composition comprises, consists of, and/or consists essentially of a film former such as a cellulose ether, e.g., hydroxypropylmethylcellulose; an extender, such as polycarbohydrates, e.g. maltodextrin; and optionally a plasticizer, such as glycols, e.g., polyethylene glycol; and may optionally be substantially free of thickeners such as hydrocolloids, e.g. xanthan gum.

An alternative gelatinous material comprises, consists of, and/or consists essentially of: a) carrageenan; and b) sucralose, as described in copending application Ser. No. 10/176,832, filed Jun. 21, 2002, published as US 2003-0108607 A1, which is incorporated herein by reference.

A further alternative gelatinous composition is comprised of, consisting of, and/or consisting essentially of: a) a film former selected from the group consisting of waxy maize starch, tapioca dextrin, derivative of a waxy maize starch, derivative of a tapioca dextrin, and mixtures thereof; b) a thickener selected from the group consisting of sucrose, dextrose, fructose, and mixtures thereof; and c) a plasticizer, wherein the composition possesses a surface gloss of at least 150 when applied via dip coating to a substrate.

Another embodiment is directed to a gelatinous composition comprised of, consisting of, and/or consisting essentially of: a) a hydroxypropyl starch film former; b) a thickener selected from the group consisting of kappa carrageenan, iota carrageenan, maltodextrin, gellan gum, agar, gelling starch, and derivatives and mixtures thereof; and c) a plasticizer, wherein the composition possesses a surface gloss of at least 150 when applied via dip coating to a substrate. Both embodiments are described in copending application Ser. No. 10/122,531, filed Apr. 15, 2002, published as US 2003-0072731 A1, which is incorporated herein by reference.

A further gelatinous composition is comprised of, consisting of, and/or consisting essentially of a film forming composition comprised of, consisting of, and/or consisting essentially of, based upon the total dry solids weight of the composition: a) from about 10 percent to about 70 percent of a film former comprised of a polymer or copolymer of (meth)acrylic acid or a derivative thereof, or a mixture of the polymer or copolymer of (meth)acrylic acid or a derivative thereof; b) from about 2 percent to about 20 percent of a primary plasticizer comprised of a paraben; and c) from about 1 percent to about 50 percent of a secondary plasticizer selected from the group consisting of polyvinylpyrrolidone, polyethylene glycol 300, polyethylene glycol 400, pharmaceutically acceptable salts thereof, and mixtures thereof; wherein the composition possesses a surface gloss of at least 150 gloss units when applied via dip coating to a substrate.

Another embodiment is a gelatinous composition comprised of, consisting of, and/or consisting essentially of, based upon the total dry solids weight of the composition: a) from about 10 percent to about 70 percent of a film former comprised of a polymer or copolymer of (meth)acrylic acid or a derivative thereof, or a mixture of the polymer or copolymer of (meth)acrylic acid or a derivative thereof; and b) from about 3 percent to about 70 percent of a plasticizer selected from the group consisting of triacetin, acetylated monoglyceride, rape oil, olive oil, sesame oil, acetyltributyl citrate, glycerin sorbitol, diethyloxalate, diethylmalate, diethyl fumarate, dibutyl succinate, diethylmalonate, dioctylphthalate, dibutylsuccinate, triethylcitrate, tributylcitrate, glyceroltributyrate, propylene glycol, polyethylene glycols, hydrogenated castor oil, fatty acids, substituted triglycerides and glycerides, methylparaben, ethyl paraben, propylparaben, butyl paraben, polyvinylpyrrolidone, polyethylene glycol 300, polyethylene glycol 400, and pharmaceutically acceptable salts thereof and mixtures thereof, wherein the composition possesses a surface gloss of at least about 150 gloss units when applied via dip coating to a substrate. Each of the foregoing (meth)acrylic (co)polymer compositions is described in copending application Ser. No. 10/211,139, filed Aug. 2, 2002, which is incorporated herein by reference.

As used herein, "substantially gelatin-free" shall mean less than about 1 percent, e.g. less than about 0.5 percent, of gelatin in the composition, and "substantially free of thickeners" shall mean less than about percent, e.g. less than about 0.01 percent, of thickeners in the composition.

One preferred process of manufacturing intermediate dosage form 20 begins by compressing or compacting a tablet core 10 into the desired shape of the medicament. As used herein, "compact, compacting, or compacted" and "compress, compressing, or compressed" may be used interchangeably to describe the commonly used process of compacting powders into tablets via conventional pharmaceutical tableting technology as well known in the art. One typical such process employs a rotary tablet machine, often referred to as a "press" or "compression machine", to compact the powders into tablets between upper and lower punches in a shaped die. This process produces a core having two opposed faces, formed by contact with an upper and lower punch, and having a bellyband formed by contact with a die wall. Typically such compressed tablets will have at least one dimension of the major faces at least as long as the height of the bellyband area between the major faces. Alternately, processes have been disclosed in the prior art to enable the "longitudinal compression" of tablet cores. When longitudinally compressed tablets are employed, it has been found that an aspect ratio (height between the major faces to width or diameter of the major faces) from about 1.5 to about 3.5, e.g. about 1.9 facilitates handling.

Tablets are typically compacted to a target weight and "hardness". Hardness is a term used in the art to describe the diametrical breaking strength as measured by conventional pharmaceutical hardness testing equipment, such as a Schleuniger Hardness Tester. In order to compare values across differently sized tablets, the breaking strength is normalized for the area of the break (which may be approximated as tablet diameter times thickness). This normalized value, expressed in kp/cm2, is sometimes referred in the art as "tablet tensile strength." A general discussion of tablet hardness testing is found in Leiberman et al., *Pharmaceutical Dosage Forms—Tablets*, Volume 2, 2nd ed., Marcel Dekker Inc., 1990, pp. 213-217, 327-329, which is incorporated by reference herein.

Gelatinous coatings 24 are provided by inserting one end 12 of core 10 into collets, immersing the exposed end 12 into a selected gelatinous material, and repeating the steps with respect to the opposing end 12 of core 10. One method for practicing such a process is described in U.S. Pat. No. 5,234,099, which is incorporated herein by reference. The gelatinous coatings 24 are provided in such a way that gelatinous coatings 24 do not meet, and in fact, form a visually discernible gap or band 26 around the non-longitudinal circumference of core 10. Alternatively, when producing a tablet form, the gap would be provided along and around the bellyband. In the preferred embodiment, subcoating 22 is exposed to the environment due to the gap or band region 26. Generally, the minimum attainable gap width is governed by machine processing tolerances. The current positioning tolerance for conventional gel-dipping equipment is about +/−0.015 inches. Results of sensory evaluation indicate that for the gap width range of 0.088 to 0.135 inches, the slipperiness of the dosage form not effected, and panelists cannot detect a height transition, i.e. "step-up" from the subcoating band to the gel-dipped ends.

An alternative means for applying gelatinous coating 24 is by shrinking wrapping opposing gelatin caps onto the substrate. Shrink wrap process technology is known and described in U.S. Pat. Nos. 6,126,767, 5,415,868, 5,824,338, 5,089,270, 5,213,738, all assigned to Perrigo and incorporated by reference herein and U.S. Pat. Nos. 5,317,849, 5,609,010, 5,460,824, 6,080,426, 6,245,350, 5,464,631, 5,795,588 and 5,511,361.

In certain preferred embodiments, intermediate dosage form 20 produced in any of the methods described above is subsequently subjected to a mechanical or laser drilling process. A transversely excited atmosphere (TEA) laser is a preferred device for this step, particularly when used in conjunction with known tablet conveying devices, such as those commercially available from Hartnett.

In one embodiment, subcoated and short-dipped gelcaps are fed into a primary hopper, from which they flow via a chute into the original hopper of a "Delta" printer, available from R. W. Hartnett Company. From the original hopper, the gelcaps fall in an upright orientation, i.e. the longitudinal axis is oriented vertically, into carrier links, and are conveyed upwards at about a 45-degree angle.

The gelcaps in the carrier links are conveyed between rubber impression rolls, which can be set at an "open" position, or a "printing" position. The gelcaps in the carrier links are then conveyed through a "drilling section", in which a laser beam is rapidly pulsed, as often as every 10 microseconds, to coincide with the gelcaps passing therethrough.

The source of the laser beam is an "Impact 2015" Transverse Excited Atmosphere C02 laser available from Lumonics Inc. The laser initially emits a 1-inch square beam having 4 Joules of energy towards a turning mirror that redirects the beam 90 degrees (upward) into a series of turning mirrors and a spherical field lens that reduces the beam from 1 inch by 1 inch to about 0.75 inch by 0.75 inch. The focused beam continues towards another turning mirror and then passes through a stainless steel mask with openings that allows only a portion of the beam to continue. The actual configuration of series the lenses and mirrors is not essential to the invention and is dictated primarily by space and cost considerations.

After passing through the mask, the patterned beam is redirected by a series of turning mirrors into a final focusing lens that reduces the size of the patterned beam about 5 times. The reduced, patterned beam ultimately strikes the gelcaps passing through the "drilling section", causing the subcoating to be ablated and form shaped openings in a pattern determined by the mask. Adjusting the height of the final turning mirror can modify the striking position of the patterned beam. Mirrors and lenses are commercially available from companies, such as LightMachinery, Inc.

FIG. 3 illustrates final dosage form 30 having ends 12 coated with gelatinous coatings 24 that form a gap 26. Openings 32 are provided in gap 26 that exposes an overcoated exterior surface of core 10. In one embodiment, the mechanical drill or laser produces at least one, preferably, a plurality of openings or holes 32 entirely through subcoating 22 to expose core 10. In another embodiment, the mechanical drill or laser produces at least one, preferably a plurality of openings 32 through subcoating 22, one gelatinous coating 24, both gelatinous coatings 24, or combinations thereof. The preferred embodiment provides a plurality of openings 32 only through subcoating 22. In certain optional embodiments, openings 32 are large enough to be visible to the naked human eye. In this case, those skilled in the art can appreciate the advantage of using subcoating 22 and/or gelatinous coating 24 having a color that is different from that of overcoated core 10 in order to highlight the presence of openings 32.

The color difference can result from inclusion of a colorant or coloring agent in subcoating 22 and/or gelatinous coating 24. In an alternative embodiment, the colorant or coloring agent is incorporated into compacted material used to make core 10, while subcoating 22 and/or gelatinous coatings 24 have one or more different colors from core 10.

A still further embodiment is a final dosage form 30 having openings 32 through subcoating 22 and/or one or more gelatinous coatings 24 that are not visually highlighted. Such an embodiment has subcoating 22 and, optionally, one or more gelatinous coatings 24 that are transparent. Alternatively, subcoating 22 and, optionally, one or more gelatinous coatings 24 have the same or similar color as overcoated core 10. An uncolored core 10 has a generally white color, which can be matched by the use of various white pigments, such as titanium dioxide. Alternatively, core 10 can be modified to include a color other than white, which also can be matched by the colorants or coloring agents provided in or over subcoating 22 and/or the gelatinous coatings 24.

An additional embodiment can be a final dosage form 30 that includes printed material meant to appear as holes or openings 32. Such an embodiment would not exhibit all of the advantages of the present invention, though having a visually similar appearance.

Gap or band region 26 can be off-center or centered on final dosage form 30. In one embodiment, as to the elongated tablet shaped core 10, gap 26 has a width of about 80 to 120 mils. Gap 26 can alternatively be expressed in terms of the percentage of the length of the elongated tablet as measured along its longest axis. Gap 26 can be characterized in such a case as being about 5% to about 33%, e.g. about 7% to about 25%, say about 10% to about 15%, the length of the elongated tablet. As the gap becomes too small, the level of improved dissolution diminishes, the area for providing openings to the core is reduced, and the visual effects of the gaps disappear. Additionally, as the gap becomes too large, some of the consumer preferences, such as swallowability, for the gelcap dosage forms may be compromised. The percentage of the surface of the core covered with the gelatinous material would be inverse of the percentage of the gap width for the tablet.

The medicaments manufactured according to the present invention, therefore, provide the desired shape, swallowability and appearance for a solid dosage form that substantially eliminates the tamperability of the medicament. Further, the discontinuous gel coating and modified subcoating provide improved dissolution and disintegration properties, but surprisingly does not compromise swallowability of the dosage form.

A still further embodiment is a final dosage form 30 having a subcoating 22 at a level of not more than about 3.0%, e.g. not more than about 2.5%, or not more than about 2.1%, say about 2% relative to the weight of the uncoated core; and/or one or more gelatinous coatings 24 that form a gap 26, wherein the width of gap 26 is at least about 5% of the overall length of the uncoated core, and wherein gelatinous coatings 24 are substantially free of visible "bubble" defects. A substantial limitation with previous generations of gel-dipped dosage forms having overlapping or abutting gelatinous coatings was the occurrence of bubble defects. Without wishing to be bound by theory, it is believed that air from the compacted core migrated through the subcoating towards the surface of the dipped gelatinous coating, causing a visible defect. Previous attempts to reduce the subcoating level below about 3.5% based on the weight of the uncoated compacted core resulted in unacceptable levels of bubble defects.

It has surprisingly been found that the non-continuous gelatinous coatings of the present invention enable elegant finished dip-coated dosage forms at subcoating levels less than 3.6%, e.g. not more than about 3.0%, or not more than about 2.5%, or not more than about 2.1%, say not more than about 2%, based on the weight of the uncoated core, wherein said dip-coated dosage form is substantially free of visible bubble defects. As used herein, substantially free of bubble defects shall mean not more than 4 tablets per hundred, e.g. not more than 1 tablet per hundred, say not more than one tablet per thousand, have visible defects greater than or equal to 2 mm in diameter, and not more than 13 tablets per hundred, e.g. not more than 3 tablets per hundred, or not more than 1 tablet per hundred, say not more than 2 tablets per thousand have visible defects less than 2 mm in diameter.

It will become apparent to those skilled in the art that various modifications to the preferred embodiments of the invention can be made by those skilled in the art without departing from the spirit or scope of the invention as defined by the appended claims.

EXAMPLES

Example 1 (Comparative) Commercially Available Caplets

Acetaminophen (500 milligrams) film-coated tablets (Extra Strength TYLENOL® Caplets) are obtained from the manufacturer, McNeil Consumer & Specialty Pharmaceuticals division of McNeil-PPC, Inc. for the purpose of comparative dissolution testing (see Example 7).

Example 2 (Comparative) Preparation of Conventional Gelcaps

2A.) Preparation of Uncoated Compacted Cores for Conventional Gelcaps

Compacted cores are prepared in accordance with the procedure set forth in Example 1 of U.S. Pat. No. 5,658,589 ("589 patent"), which is incorporated by reference herein.

2B) Preparation of Subcoating Dispersion for Conventional Gelcaps

An aqueous dispersion containing the ingredients set forth in Table A is prepared by mixing the HPMC and castor oil into half of the water at slow mixer speed and a temperature 80° C. in a stainless steel jacketed vacuum tank under ambient conditions, then continuing to mix at "fast" speed for 15 minutes. The second half of the water is then added to the tank, with continued mixing at "slow" speed. The solution is then deaerated by vacuum, and cooled to a temperature of 35° C., with continued mixing at "slow" speed. Mixing is then discontinued, vacuum released, and the solution is transferred to a pressure pot for spraying onto the tablet cores.

TABLE A

Aqueous Dispersion Subcoating Composition for Comparison Gelcaps

| Ingredient | Parts* |
|---|---|
| HPMC (2910, 5 mPs) from Dow Chemical Company under the tradename, "Methocel E-5" | 61.2 |
| Castor oil | 0.24 |
| Water | 620.0 |
| Total Coating Solution | 681.44 |
| % solids in coating solution | 9% |

*expressed in terms of parts by weight unless otherwise noted

2C) Preparation of Subcoated Cores for Conventional Gelcaps

The coating dispersion is then applied onto the compressed tablets via spraying in accordance with the procedure set forth in the examples of the '589 patent. The coating dispersion is applied to the compressed cores in amount sufficient to produce an increased weight of an average of 4.5% relative to the weight of the subcoating-free compressed cores.

2D) Preparation of Colorless Gelatin-Based Dipping Dispersion

The ingredients in the table below are used to prepare a 1200 liter batch of colorless gelatin-based dipping solution. Purified water at a temperature of about 85° C. is added to a jacketed vacuum-equipped mix tank. Sodium lauryl sulfate (SLS) is added to the water, followed by Gelatin 275 Bloom and Gelatin 250 Bloom while mixing. The temperature of the mixture after addition of the gelatin blend is approximately 57° C. The gelatin solution is mixed for 10 minutes, and then deaerated under vacuum for 4 hours.

| Ingredient | Percent w/w of dispersion | Percent w/w of gelcap |
|---|---|---|
| Purified Water USP | 67.01 | — |
| Sodium Lauryl Sulfate | 0.03 | 0.006 |
| Gelatin NF (275 Bloom Skin) | 10.15 | 1.8 |
| Gelatin NF (250 Bloom Bone) | 22.80 | 4.2 |

2E) Preparation of Yellow Gelatin-Based Dipping Solution 96 kg of colorless gelatin-based dipping solution prepared according to example 2D is transferred to a jacketed mix tank. 4.30 kg of Opatint Yellow DD2125 is added. The solution is mixed at low speed for 4 hours (at ambient pressure) to deaerate while the tank is maintained at a solution temperature of about 55° C.

2F) Preparation of Red Gelatin-Based Dipping Solution 96 kg of colorless gelatin-based dipping solution prepared according to example 2D is transferred to a jacketed mix tank. 4.30 kg of Opatint Red DD1761 is added. The solution is mixed at low speed for 4 hours (at ambient pressure) to deaerate while the tank is maintained at a solution temperature of about 55° C.

2G.) Gel Dipping of Subcoated Cores for Conventional Gelcaps

Subcoated cores prepared according to the method of examples 2A-2C, above, are placed (in a plastic tote) at the tablet inlet station of the gel dipping apparatus described in U.S. Pat. No. 5,234,099, which is incorporated herein by reference in its entirety.

Yellow gel-dipping solution prepared according to example 2E herein is transferred to a first gelatin feed tank. Red gel-dipping solution prepared according to example 2F herein is transferred to a second gelatin feed tank. Material from each gelatin feed tank is allowed to flow into a separate dip pan. A first end of each subcoated core is dipped into the yellow gel-dipping solution, and a second end of each subcoated core is dipped into the red gel-dipping solution, according to the method and using the apparatus described in U.S. Pat. No. 5,234,099. The gel-dipping operation is carried out using the following operating limits:

Supply air temperature: 26-32° C.
Supply air dew point: 6-12° C.
Supply air volume: 9450-10550 CFM
Dip area temperature 15-25° C.
Dip area air volume 230-370 CFM
Dip pan Temperatures (red and yellow): 44-46° C.
Yellow gel dipping solution viscosity: 525-675 cps
Red gel dipping solution viscosity: 675-825 cps
Depth of dip to cutline (yellow): 0.406"-0.437"
Depth of dip to cutline (red): 0.375"-0.406"
Moisture content (% loss on drying at 150° C.) of finished gelcaps: 2.0-3.0%

Example 3: Preparation of Subcoated Gelcap Cores at 3.0 and 4.5% Coating Levels Compressed cores are prepared according to the method set forth in Example 1A herein. 316 kg of the compressed cores are loaded into a 48-inch diameter side vented coating pan (Accela Cota) equipped with 4 suitable [model JAU available from Spraying Systems Inc.] 2-fluid spray guns at a gun to tablet bed distance of approximately 12 inches.

An aqueous subcoating dispersion is prepared according to the method of Example 2B. A 160 kg quantity of subcoating dispersion 2B is metered into a pressurized coating dispersion tank equipped with a mixer and vacuum. 1.17 kg of Opatint Red DD1761 is added with mixing at 700 rpm for 10 minutes. The red subcoating dispersion is deaerated for 10 minutes under vacuum.

The red subcoating dispersion is then sprayed onto the compressed cores in an amount (107.4 kg) sufficient to produce an increased weight of an average of 3.0% relative to the weight of the uncoated compressed cores. A 20 kg sample of the 3.0% subcoated cores is removed. The 3.0% subcoated cores are referred to herein as sample "3A". The remainder of the panload is then further coated with an additional 53.7 kg of subcoating dispersion, to obtain a total increased weight of an average of 4.5% relative to the weight of the uncoated compressed cores. The 4.5% subcoated cores are referred to herein as sample "3B".

The red subcoating dispersion is mixed at 300 rpm throughout the spraying process. The coating process is conducted, using the following parameters:

Coating dispersion tank pressure: 74.0-74.5 PSI
Atomizing Air pressure: 71.9-73.9 PSI
Dispersion spray rate: 0.63-0.66 kg/minute
Supply Air Volumetric Flow Rate: 4190-4319 cubic feet per minute
Coating pan pressure: −0.25-0.30 in. We
Supply air temperature: 69.3-80.4° C.
Exhaust air Temperature: 62.3° C.-64.6° C.
Pan speed (first 40 kg of solution): 4.11 rpm
Pan speed (after first 40 kg of solution): 6.92 rpm Example 4: Preparation of Subcoated Gelcap Cores at 2.0% Coating Level 316 kg of compressed cores prepared according to the method set forth in Example 1A herein are loaded into a 48-inch diameter side vented coating pan (Accela Cota) equipped with 4 suitable [model JAU, available from Spraying Systems Inc.] 2-fluid spray guns at a gun to tablet bed distance of approximately 12 inches.

An aqueous subcoating dispersion is prepared according to the method of Example 2B. A 160 kg quantity of subcoating dispersion 2B is metered into a pressurized coating dispersion tank equipped with a mixer and vacuum. 2.63 kg of Opatint Red DD1761 is added with mixing at 700 rpm for 10 minutes. The red subcoating dispersion is deaerated for 10 minutes under vacuum.

The red subcoating dispersion is then sprayed onto the compressed cores in an amount (72.2 kg) sufficient to produce an increased weight of an average of 2.0% relative to the weight of the uncoated compressed cores. The 2.0% subcoated cores are referred to herein as sample "4".

The red subcoating dispersion is mixed at 300 rpm throughout the spraying process. The coating process is conducted, using the following parameters:

Coating dispersion tank pressure: 75.0 PSI
Atomizing Air pressure: 70.2-70.6 PSI
Dispersion spray rate: 0.62-0.65 kg/minute
Supply Air Volumetric Flow Rate: 4179-4182 cubic feet per minute
Coating pan pressure: −0.15-0.26 in. We
Supply air temperature: 70.8-81.1° C.
Exhaust air Temperature: 61.5° C.-62.7° C.
Pan speed (first 40 kg of solution): 3.92 rpm
Pan speed (after first 40 kg of solution): 6.82 rpm Example 5: Gel Dipping of Subcoated Cores to Prepare the Dosage Form of the Invention SA) 96 kg of colorless gelatin-based dipping solution prepared according to example 2D is transferred to a jacketed mix tank. 4.3 kg of Opatint Blue DD-10516 is added. The solution is mixed at low speed for 4 hours (at ambient pressure) to deaerate while heating the tank to maintain a solution temperature of about 55° C.

Blue gel-dipping solution is transferred to a first gelatin feed tank. Blue gel-dipping solution is transferred to a second gelatin feed tank. Material from each gelatin feed tank is allowed to flow into a separate dip pan.

5B) Subcoated cores prepared according to Example 4 (2.0% subcoating level), are transferred to the hopper of the gel-dipping apparatus described in U.S. Pat. No. 5,234,099.

A first end of each subcoated core is dipped into blue gel-dipping solution, and a second end of each subcoated core is dipped into the second blue gel-dipping solution, according to the method and using the apparatus described in U.S. Pat. No. 5,234,099. The gel-dipping operation is carried out using the following operating limits:

Supply air temperature: 28° C.
Supply air dew point: 9° C.
Supply air volume: 10013 CFM
Dip area temperature 21° C.
Dip area air volume 300 CFM
Dip pan Temperatures (1st and 2nd): 44.6-44.9° C.
Blue (1) gel-dipping solution viscosity: 680 cps
Blue (2) gel-dipping solution viscosity: 793 cps
Depth of dip to cutline (first blue end): 0.320"-0.333"
Depth of dip to cutline (second blue end): 0.320"-0.335"
Moisture content (% loss on drying at 150° C.) of finished gelcaps: 2.0%
Gel-dipped coating level (% by weight of subcoated cores): 5.3%

5C) The "short-dipped" gelcaps are then transferred to the hopper of a Hartnett Delta Printer equipped with a TEA-Laser, as described previously herein. A plurality of openings is ablated into the exposed subcoating portion in a pattern, as shown in FIG. 3.

Example 6: Gel-Dipping of Subcoated Cores from Example 3 (4.5% Subcoating Level)

6A) Subcoated cores prepared according to example 3 are dipped in blue gel-dipping solution according to the method of Examples 5A&B herein, leaving a band of exposed red subcoating.

6B) A plurality of openings is ablated into the exposed subcoating portion in a pattern, according to the method of Example 5C herein.

Example 7

Comparative Dissolution Data for 500 mg Acetaminophen Solid Dosage Forms

|  | Time (minutes): | | | | | |
| --- | --- | --- | --- | --- | --- | --- |
|  | '3 | 6 | 9 | 12 | 15 | 30 |
| Ex. 1 Caplet | 82 | 97 | 99 | 100' | 100 | 100 |
| Ex. 2A Uncoated Core | 81 | 99 | 100 | 101 | 101 | 101 |
| Ex. 2C Subcoated Core (4.5%) | 4 | 84 | 99 | 101 | 101 | 102 |
| Ex. 2G Gelcap | 0 | 51 | 94 | 99 | 100 | 100 |
| Ex. 3B Subcoated Core (4.5%) | 17 | 90 | 98 | 99 | 99 | 100 |
| Ex. 6A Short dipped from ex. 3B | 0 | 47 | 91 | 95 | 97 | 98 |
| Ex. 6B: 6A with laser openings | 63 | 95 | 98 | 99 | 99 | 100 |
| Ex. 4 Subcoated Core (2.0%) | 77 | 96 | 98 | 99 | 99 | 99 |
| Ex. 5B Short dipped from Ex. 4 | 40 | 89 | 96 | 97 | 98 | 99 |
| Ex. 5C: 5B with laser openings | 80 | 95 | 97 | 98 | 98 | 99 |

Example 8: Sensory Evaluation of Gap Width

Short-dipped gelcaps prepared according to example 5B, were sorted according to the width of the exposed subcoating band, and grouped into the following categories:

| Sample | min bandwidth (inches) | max bandwidth (inches) |
|--------|------------------------|------------------------|
| c      | 0.08766                | 0.09766                |
| A      | 0.09846                | 0.10051                |
| E      | 0.1011                 | 0.11535                |
| D      | 0.11206                | 0.13454                |
| B      | 0.14008                | 0.16916                |

One sample from each gapwidth category was then evaluated by each of 11 panelists, and rated according to the following criteria:
1=Cannot detect a texture difference between exposed subcoating band and gel-dipped ends
2=some texture difference if scrutinized, but slipperiness of dosage form not effected, and cannot detect a height transition, i.e. "step-up" from the subcoating band to the gel-dipped ends
3=definite perceptible texture transition between gel-dipped ends and exposed subcoating band
4=Can feel a difference in height, i.e. the "step up" from the subcoating band to the gel-dipped ends
Results of the evaluation were as follows:

|   | P1 | P2 | P3 | P4 | P5 | P6 | P7 | P8 | pg | P10 | P11 | AvQ  | Stdev |
|---|----|----|----|----|----|----|----|----|----|-----|-----|------|-------|
| c | 1  | 1  | 1  | 1  | 1  | 1  | 2  | 2  | 2  | 2   | 2   | 1.45 | 0.52  |
|   | 1  | 1  | 1  | 1  | 1  | 1  | 2  | 2  | 2  | 2   | 1   | 1.36 | 0.50  |
| E | 1  | 1  | 1  | 1  | 1  | 1  | 2  | 2  | 1  | 2   | 2   | 1.36 | 0.50  |
| D | 1  | 1  | 1  | 1  | 1  | 2  | 2  | 2  | 2  | 1   | 2   | 1.45 | 0.52  |
| B | 1  | 1  | 1  | 1  | 2  | 2  | 3  | 3  | 2  | 1   | 1   | 1.64 | 0.81  |

Results of this evaluation indicate that for the gap width range of 0.088 to 0.135 inches, the slipperiness of the dosage form not effected, and panelists cannot detect a height transition, i.e. "step-up" from the subcoating band to the gel-dipped ends.

Example 9—Surface Gloss Measurement of Coated Tablets

Tablets described below were tested for surface gloss using an instrument available from TriCor Systems Inc. (Elgin, Ill.) under the tradename, "Tri-Cor Model 805A/806H Surface Analysis System" generally in accordance with the procedure described in "TriCor Systems WGLOSS 3.4 Model 805A/806H Surface Analysis System Reference Manual" (1996), which is incorporated by reference herein, except as modified below.

The instrument utilized a CCD camera detector, employed a flat diffuse light source, compared tablet samples to a reference standard, and determined average gloss values at a sixty (60) degree incident angle. During operation, the instrument generated a gray-scale image, wherein the occurrence of brighter pixels indicated the presence of more gloss at that given location. The instrument also incorporated software that utilized a grouping method to quantify gloss, i.e., pixels with similar brightness were grouped together for averaging purposes.

The "percent full scale" or "percent ideal" setting (also referred to as the "percent sample group" setting), was specified by the user to designate the portion of the brightest pixels above the threshold that will be considered as one group and averaged within that group. "Threshold", as used herein, is defined as the maximum gloss value that will not be included in the average gloss value calculation. Thus, the background, or the non-glossy areas of a sample were excluded from the average gloss value calculations. The method disclosed in K. Fegley and C. Vesey, "The Effect of Tablet Shape on the Perception of High Gloss Film Coating Systems", which is available at www.colorcon.com as of 18 Mar. 2002 and incorporated by reference herein, was used in order to minimize the effects resulting from different tablet shapes, and thus report a metric that was comparable across the industry. (Selected the 50% sample group setting as the setting which best-approximated analogous data from tablet surface roughness measurements).

After initially calibrating the instrument using a calibration reference plate (190-228; 294 degree standard; no mask, rotation 0, depth 0), a standard surface gloss measurement was then created using gel-coated caplets available from McNeil-PPC, Inc. under the tradename, "Extra Strength Tylenol Gelcaps." The average gloss value for a sample of 112 of such gel-coated caplets was then determined, while employing the 25 mm full view mask (190-280), and configuring the instrument to the following settings:
Rotation: 0
Depth: 0.25 inches
Gloss Threshold: 95
% Full Scale: 50%
Index of Refraction: 1.57
The average surface gloss value for the reference standard was determined to be 269, using the 50% ideal (50% full scale) setting. Commercially available gel coated tablets were tested in accordance with the above procedure. The results are summarized in table below.

TABLE

| Gloss values of commercially available coated tablets | | | | | |
|---|---|---|---|---|---|
| Product | Excedrin ** Aspirin free Caplets (red) | Excedrin ** Migraine Geltab (green side) | Excedrin ** Migraine Geltab (white side) | Extra Strength Tylenol Geltabs * (yellow side) | Extra Strength Tylenol Geltabs * (red side) |
| Type of coating | Sprayed film | Gelatin enrobed | Gelatin enrobed | Dipped | Dipped |
| No. of tablets tested | 40 | 10 | 10 | 112 | 112 |
| Gloss Value(% ideal at 50) | 119 | 270 | 264 | 268 | 268 |

* Available from McNeil-PPC, Inc.
** Available from Bristol-Myers, Squibb, Inc.

We claim:
1. A dosage form, comprising:
a core, wherein the core comprises at least one active ingredient;
a subcoating, wherein the subcoating is applied to an exterior surface of the core;

a first gelatinous coating applied to a first end of the core;

a second gelatinous coating applied to a second end of the core;

wherein the first gelatinous coating and the second gelatinous coating are applied to the first end of the core and the second end of the core, respectively, after the subcoating is applied to the exterior surface of the core;

wherein the first gelatinous coating and the second gelatinous coating are separated from one another and form a gap through which the subcoating is exposed, wherein the gap has a width of equal to or greater than 7% to about 25% of an overall length of the core.

2. The dosage form according to claim 1, wherein the subcoating is applied to the entire exterior surface of the core.

3. The dosage form of claim 1, wherein the one or more active ingredients is selected from the group consisting of pseudoephedrine, phenylpropanolamine, chlorpheniramine, dextromethorphan, diphenhydramine, astemizole, terfenadine, fexofenadine, loratadine, desloratadine, cetirizine, mixtures thereof, and pharmaceutically acceptable salts, esters, isomers, and mixtures thereof.

4. The dosage form of claim 3, wherein the one or more active ingredients is selected from fexofenadine and pharmaceutically acceptable salts thereof.

5. A method for producing a dosage form comprising:
a) coating an exterior surface of a compressed tablet having two opposing ends with a subcoating to form a subcoated compressed tablet;
b) providing one end of the subcoated compressed tablet with a gelatinous material; and
c) providing a second end of the subcoated compressed tablet with a gelatinous material;
wherein the gelatinous coatings resulting from steps b) and c) form a gap that exposes an exterior surface of the subcoated compressed tablet from step a), wherein a width of said gap is equal to or greater than 7% to about 25% of an overall length of the core.

6. The method according to claim 5, wherein the subcoating is applied to the entire exterior surface of the compressed tablet.

7. The method of claim 5, wherein the one or more active ingredients is selected from the group consisting of pseudoephedrine, phenylpropanolamine, chlorpheniramine, dextromethorphan, diphenhydramine, astemizole, terfenadine, fexofenadine, loratadine, desloratadine, cetirizine, mixtures thereof, and pharmaceutically acceptable salts, esters, isomers, and mixtures thereof.

8. The method of claim 7, wherein the one or more active ingredients is selected from fexofenadine and pharmaceutically acceptable salts thereof.

9. A dosage form comprising:
a) a core having an exterior surface and first and second ends and comprising one or more active ingredients;
b) a subcoating, wherein the subcoating is applied to the exterior surface of the core to form a subcoated core;
c) a first gelatinous coating over at least part of the subcoated core; and
d) a second gelatinous coating over at least part of the subcoated core;
wherein the first and second gelatinous coatings are provided on said first and second ends of the subcoated core; wherein the total level of said first and second gelatinous coatings is from about 3 to about 10 weight percent based on the weight of the core; wherein said first and second gelatinous coatings form a gap through which the subcoated core is exposed; wherein the width of gap is from more than 7% to about 25% of the overall length of the subcoated core.

10. A method of treatment, comprising administering a dosage form, wherein said dosage form comprises:
a) a core having an exterior surface and first and second ends, wherein the core comprises one or more pharmaceutically active ingredients, cellulose or a derivative of cellulose, pregelatinized starch, and magnesium stearate;
b) a subcoating, wherein the subcoating is applied to the exterior surface of the core to form a subcoated core;
c) a first gelatinous coating over at least part of the subcoated core; and
d) a second gelatinous coating over at least part of the subcoated core;
wherein the first and second gelatinous coatings are provided on the first and second ends of the subcoated core; wherein the first and second gelatinous coatings form a gap through which the subcoated core is exposed, wherein the gap has a width of greater than 7% to about 25% of the length of the subcoated core, wherein the gap does not affect swallowability of the dosage form; and wherein the first and second gelatinous coatings each comprise gelatin.

\* \* \* \* \*